(12) United States Patent
He et al.

(10) Patent No.: US 12,087,451 B2
(45) Date of Patent: Sep. 10, 2024

(54) CONTACT TRACING PRE-SCREENING METHOD FOR INFECTIOUS DISEASE SUSCEPTIBLE PEOPLE BASED ON WIFI MATCHING

(71) Applicant: ZHEJIANG UNIVERSITY, Zhejiang (CN)

(72) Inventors: Shibo He, Zhejiang (CN); Chao Li, Zhejiang (CN); Ruiwei Yu, Zhejiang (CN); Mincheng Wu, Zhejiang (CN); Jiming Chen, Zhejiang (CN); Peng Cheng, Zhejiang (CN); Yu Liu, Zhejiang (CN)

(73) Assignee: ZHEJIANG UNIVERSITY, Zhejiang (CN)

( * ) Notice: Subject to any disclaimer, the term of this patent is extended or adjusted under 35 U.S.C. 154(b) by 0 days.

(21) Appl. No.: 17/925,317

(22) PCT Filed: Apr. 21, 2022

(86) PCT No.: PCT/CN2022/088158
§ 371 (c)(1),
(2) Date: Nov. 15, 2022

(87) PCT Pub. No.: WO2023/197350
PCT Pub. Date: Oct. 19, 2023

(65) Prior Publication Data
US 2024/0257985 A1    Aug. 1, 2024

(30) Foreign Application Priority Data
Apr. 14, 2022 (CN) .......................... 202210413620.2

(51) Int. Cl.
*G16H 50/80* (2018.01)
*H04W 8/18* (2009.01)
*H04W 12/02* (2009.01)

(52) U.S. Cl.
CPC .............. *G16H 50/80* (2018.01); *H04W 8/18* (2013.01); *H04W 12/02* (2013.01)

(58) Field of Classification Search
None
See application file for complete search history.

(56) References Cited

U.S. PATENT DOCUMENTS

| 2019/0252078 A1 | 8/2019 | Schubert et al. |
| 2021/0050116 A1* | 2/2021 | Sabeti .................... G06N 7/01 |

(Continued)

FOREIGN PATENT DOCUMENTS

| CN | 104778642 | 7/2015 |
| CN | 111354472 | 6/2020 |

(Continued)

OTHER PUBLICATIONS

Ng et al. "COVID-19 and Your Smartphone: BLE-Based Smart Contact Tracing". IEEE Systems Journal, vol. 15, No. 4, Dec. 2021 (Year: 2021).*

(Continued)

*Primary Examiner* — Jonathan Ng
(74) *Attorney, Agent, or Firm* — JCIPRNET

(57) ABSTRACT

Disclosed in the present invention is a contact tracing pre-screening method for infectious disease susceptible people based on WiFi matching. In the method, based on WiFi connection records of a user and a list of anonymous identification codes of confirmed users collected by a mobile device, a judgment on whether a user has an infection risk is given through the steps of record matching, information compression, dangerous WiFi database construction, coincidence rate calculation between the user and a dangerous WiFi, etc. Data required by this method is easy to be obtained for general smart mobile devices, and no special application program is required. Compared with traditional (Continued)

contact tracing methods based on GPS and Bluetooth, this method provides another dimension of information without using an additional device and sensitive data, has higher operating efficiency, and can help to carry out contact tracing more comprehensively and efficiently.

5 Claims, 2 Drawing Sheets

(56) References Cited

U.S. PATENT DOCUMENTS

| | | | | |
|---|---|---|---|---|
| 2021/0313074 | A1* | 10/2021 | Mesirow | H04W 4/029 |
| 2021/0338973 | A1* | 11/2021 | Poltorak | G06V 10/764 |
| 2022/0030382 | A1* | 1/2022 | Klasson | G16H 10/60 |
| 2022/0037029 | A1* | 2/2022 | Wu | G16H 50/50 |
| 2022/0285036 | A1* | 9/2022 | Merjanian | G16H 50/80 |

FOREIGN PATENT DOCUMENTS

| | | |
|---|---|---|
| CN | 111354473 | 6/2020 |
| CN | 111446006 | 7/2020 |
| WO | 2021167159 | 8/2021 |

OTHER PUBLICATIONS

E. Hernández-Orallo, P. Manzoni, C. T. Calafate and J.-C. Cano, "Evaluating How Smartphone Contact Tracing Technology Can Reduce the Spread of Infectious Diseases: The Case of COVID-19," in IEEE Access, vol. 8, pp. 99083-99097, 2020, doi: 10.1109/Access. 2020.2998042 (Year: 2020).*

Trivedi et al "WiFiTrace: Network-based Contact Tracing for Infectious Diseases Using Passive WiFi Sensing". arXiv:2005.12045 (Year: 2005).*

"International Search Report (Form PCT/ISA/210) of PCT/CN2022/ 088158," mailed on Dec. 29, 2022, with English translation thereof, pp. 1-4.

"Written Opinion of the International Searching Authority (Form PCT/ISA/237) of PCT/CN2022/088158," mailed on Dec. 29, 2022, with English translation thereof, pp. 1-6.

* cited by examiner

CONTACT TRACING PRE-SCREENING METHOD FOR INFECTIOUS DISEASE SUSCEPTIBLE PEOPLE BASED ON WIFI MATCHING

CROSS-REFERENCE TO RELATED APPLICATION

This application is a 371 of international application of PCT application serial no. PCT/CN2022/088158, filed on Apr. 21, 2022, which claims the priority benefit of China application no. 202210413620.0, filed on Apr. 14, 2022. The entirety of each of the above mentioned patent applications is hereby incorporated by reference herein and made a part of this specification.

TECHNICAL FIELD

The present invention relates to detection of infectious disease susceptible people, and in particular to a contact tracing pre-screening method for infectious disease susceptible people based on WiFi matching.

RELATED ART

The outbreak of the new coronavirus in early 2020 has had a great impact on the production and life of the world. As of March 2022, cumulative number of confirmed cases in the world has exceeded 470 million, and cumulative number of deaths has exceeded 6 million. The coronavirus disease (COVID-19) has been identified as one of the worst public health outbreaks in history. The new coronavirus epidemic has brought huge loss of life and property to the world, caused severe divisions among countries, societies, and groups of people, and profoundly changed the world pattern.

In the process of preventing and controlling the epidemic, contact tracing is a very critical step. In public health, the contact tracing refers to a process of identifying contacts who may have been in contact with an infected person, and subsequently collecting further information about these contacts. Since many infectious diseases, including COVID-19, need to be spread among people through respiratory transmission, contact transmission, etc., that is, contact among people occurs, early detection of these high-risk groups who have been in contact with infected people plays a very important role in timely isolation of potential infected people.

Traditional contact tracing methods mainly rely on questionnaires of infected persons, which are highly dependent on the memory of respondents, have poor reliability, and are labor-intensive and inefficient. With the development of information age, digital contact tracing technologies, such as contact tracing using applications on smart terminals, have gradually become the answer to this problem. The digital contact tracing methods usually require location data, such as GPS, WiFi, communication base stations, Bluetooth beacons, etc., and can be further divided into two types of methods according to the type of data used:

1) Methods using absolute location data: using absolute location information, such as GPS locations, locations relative to static WiFi hotspots or communication base stations, which can usually be expressed in the form of geographic coordinates. These data may not be accurate enough for infectious disease contact tracing, but a large amount of the data can reveal behavior patterns of specific users and cluster them.

2) Methods using relative location data: using relative location information, such as interaction data of two devices with Bluetooth enabled, and data relating to the use of the same public transport vehicle such as an airplane, a train, etc. The data is usually represented as pairs of data each of which relates to the same region at a certain point in time. The data is relatively more accurate, but on the one hand, it requires specific devices (such as Bluetooth devices), and on the other hand, it focuses too much on point-to-point interactions and lack overall information.

Both types of data have some practical applications. For example, a health code commonly used in China uses GPS sequence data of a user for contact judgment and tracing, while a TraceTogether service provided by the Singapore government forces citizens to download a special application that uses Bluetooth signals or wear a special Bluetooth communication device so as to carry out the contact tracing, but both schemes have their shortcomings in application: the GPS data has limited indoor accuracy, and involves sensitive information such as specific location trajectories of persons; and the Bluetooth point-to-point contact data requires large-scale use of professional equipment, which is expensive and difficult to popularize.

In view of the shortcomings of the above methods, the applicant proposes a contact tracing pre-screening method for infectious disease susceptible people based on WiFi matching.

SUMMARY OF INVENTION

Technical Problem

The purpose of the present invention is to make up for the defects of the existing application technology. By using different types of data to provide a more comprehensive contact tracing method for infectious disease susceptible people, the method can use the WiFi access records of confirmed patients having historical infectious diseases to construct a dangerous WiFi database, give a user's infection risk after obtaining daily updated user WiFi access records, and improve the efficiency of finding susceptible people.

The object of the present invention is achieved through the following technical solutions:

A contact tracing pre-screening method for infectious disease susceptible people based on WiFi matching, wherein the method comprises the following steps:

1) matching with user anonymous identification code record: obtaining a unique anonymous identification code data table of confirmed users through a database, using hive sql tool to search for WiFi connection records corresponding to the identification codes (IDs) in a total database, creating data table partitions according to dates, and saving the data table partitions as original data records with a total data time span of T days, and constructing a WiFi connection data set $R=\{R_1, R_2, \ldots, R_T\}$ of the confirmed users, wherein records of the ith day are $R_i$, and there are a total of $k_i$ records, and $R_i=\{r_{i1}, r_{i2}, \ldots, r_{ik}\}$, wherein each record $r_{ij}=(gid_{ij}, confirmDay_{ij}, mac_{ij})$, $gid_{ij}$ represents a unique anonymous identification code of a user, $confirmDay_{ij}$ represents a confirmed date of the user, and $mac_{ij}$ represents a media access control (MAC) address of an WiFi to which the user connects;

2) pre-processing the data: saving the data set R obtained in step (1) to local codes, and establishing a two-way mapping dictionary class to save storage space, creating a new referencing symbol for any string according to the number of internal stored entries after obtaining the string, using the string and the referencing symbol respectively as a key and a value to establish a mapping; establishing a code two-way mapping dictionary $dict_{user}$ for the anonymous identification codes of the users, recording the total number of the users as $N_u$, and mapping the original anonymous identification code with uniform-length of the user to a code number $u_{i_u}$, wherein $i_u$=1, 2, 3, . . . , $N_u$; establishing a code two-way mapping dictionary $dict_{wifi}$ of the WiFis, recording the total number of the WiFis as $N_w$, and mapping the original MAC address of the WiFi as a code number $w_{u_w}$, wherein $u_w$=1, 2, 3, . . . , $N_w$; recording a record data set obtained after mapping the original record data set as R;

3) constructing a dangerous WiFi database: using the record data set $\bar{R}$ after the code number mapping in step (2), recording the dangerous WiFi database as $dict_{dan}$, extracting the WiFi connection records of the confirmed users in $\bar{R}$, taking the code number $w_{u_w}$ of the WiFi in the records and putting $w_{u_w}$ in $dict_{dan}$, and recording a date in which the WiFi is recorded in the dangerous WiFi database as the current date $day_{now}$); if the WiFi already exists, updating the recording date thereof to $day_{now}$), and then deleting a record of which the difference between the recording date $day_{now}$ and the current date $day_{now}$ exceeds a dangerous WiFi disappearance threshold $thr_{dan}$;

4) judging an infection risk: recording newly acquired WiFi connection records of the users every day as $\tilde{R}$, grouping $\tilde{R}$ by the users, and for each user, matching all the connected WiFis thereof with $dict_{dan}$, and recording a coincidence rate as $r_{user}=|C_{user}|/|W_{user}|$, wherein $|C_{user}|$ is the number of WiFis in $dict_{dan}$ that the user connects to in that date, $|W_{user}|$ is the total number of WiFis that the user connects in that date, and if $r_{user}$ is higher than a judgment threshold $thr_{user}$, judging the user as a dangerous user.

Further, in the matching of the users' anonymous identification code record in step 1), the hive sql tool is used to match the unique anonymous identification code of the confirmed user with a WiFi connection record total database of all the national users, and a data record table is generated for subsequent processing of confirmed users in the data table partitions, wherein the specific implementation steps are as follows:

1.1) forming the original database consisted of two parts:
1.1.1) an information data table of confirmed users, including the anonymous identification codes (gid_confirm) of the confirmed users, confirmed dates (confirm_day); 1.1.2) a WiFi connection record data table of all the national users, including the anonymous user identification codes (gid), connected WiFi MAC addresses (mac), record generation dates (day), record generation areas (area), record generation time (hour), and WiFi connection times (times) during the record time, using the same anonymous user identification codes of the two databases as indexes, and using the hive sql tool to generate a WiFi connection record data table of the confirmed users;

wherein, the WiFi connection record data table of all the national users is partitioned according to the areas (area) and dates (day), and a target screening area (an area code thereof is AREACORE) and the start-end time (which are BEGINDAY and ENDDAY respectively) of target inspection are determined in advance when constructing the target data table so as to improve screening efficiency and reduce screening time;

1.2) using the hive sql tool to partition the target data table according to the dates as the indexes in order to prevent the subsequent processing of the WIFI connection record data table of the confirmed users from resulting in memory overflow due to the large amount of data.

Further, in the data pre-processing of step 2), the code two-way mapping dictionary is used to compress and restore the original user anonymous identification codes and the MAC addresses of the WiFis, and the specific implementation steps are as follows:

2.1) constructing the two-way mapping dictionary class (TwoWayDict), wherein after inputting an original uncompressed string, the two-way mapping of uncompressed string to compressed string and the compressed string to the uncompressed string is formed inside the code two-way mapping dictionary, that is, the uncompressed string and the compressed string are stored as the key and the corresponding value respectively to save storage space and memory in subsequent processing, and, when a prediction result is obtained, the original uncompressed string is also obtained according to the code two-way mapping dictionary;

2.2) establishing, through the above manner, two code two-way mapping dictionaries $dict_{user}$ and $dict_{wifi}$ with the anonymous identification codes of the users and the MAC addresses of the WiFis respectively.

Further, in constructing the dangerous WiFi database of step 3), the MAC addresses in historical user WiFi connection data are added to the dangerous WiFi database according to dates, and expired WiFis are dynamically deleted to reduce a false positive rate, wherein the specific implementation steps are as follows:

3.1) processing historical data, extracting the MAC addresses of the WiFis and confirmed dates in the WiFi connection records of historically confirmed users, and putting the MAC addresses and the confirmed dates into the dangerous WiFi database $dict_{dan}$, wherein $dict_{dan}$ takes the WiFi MAC address as the key and the confirmed date as the value, and, if there are duplicate MAC addresses, the one having the most recent date is selected and saved as the value;

3.2) processing daily updated data: after obtaining the daily updated data, adding the MAC addresses of the WiFis to which the confirmed users connects in that date in $dict_{dan}$ through the above method, and traversing $dict_{dan}$ after the addition; and if the difference between the confirmed date corresponding to the MAC address and the current date exceeds the dangerous WiFi disappearance threshold $thr_{dan}$, deleting the MAC address from the dangerous WiFi database.

Further, in the infection risk judgment of step 4), the daily updated user WiFi connection data is compared with the dangerous WiFi database to obtain the coincidence rate, and a judgment is made on whether a dangerous user exists according to the judgment threshold, wherein the specific steps are as follows:

4.1) after obtaining the daily updated user WiFi connection data, grouping the records according to the anonymous identification codes of the users, and calculating the coincidence rate between the WiFi connection in that date and the dangerous WiFi database, wherein a calculation formula for the coincidence rate $r_{user}$ of the user (user) is as follows:

$$C_{user} = W_{user} \cap W_{dan}$$

$$r_{user} = \frac{|C_{user}|}{|W_{user}|}$$

wherein $W_{user}$ is the WiFi connected by the user in that date, and $W_{dan}$ is the dangerous WiFi database;

if $R_{user}$ is higher than the judgment threshold $thr_{user}$, judging $R_{user}$ as a dangerous user, and carrying out key screening.

The present invention provides the contact tracing pre-screening method for infectious disease susceptible people based on WiFi matching. The method is mainly based on WiFi connection records of the users and the list of anonymous identification codes of the confirmed users collected by the mobile device, and finally gives the final dangerous user list through the steps of the record matching, information compression, dangerous WiFi database construction, coincidence rate calculation between the user and the dangerous WiFis, etc. The present invention analyzes, corrects and reduces the dimensions of the WiFi connection record data. Compared with the contact tracing method, it can save computing resources, reduce processing time and improve screening efficiency without involving private information such as location and without using additional equipment, which provides another data support having more comprehensive dimensions for the follow-up search for high-risk susceptible groups who may come into contact with the confirmed users.

DESCRIPTION OF EMBODIMENTS

Figure 1:
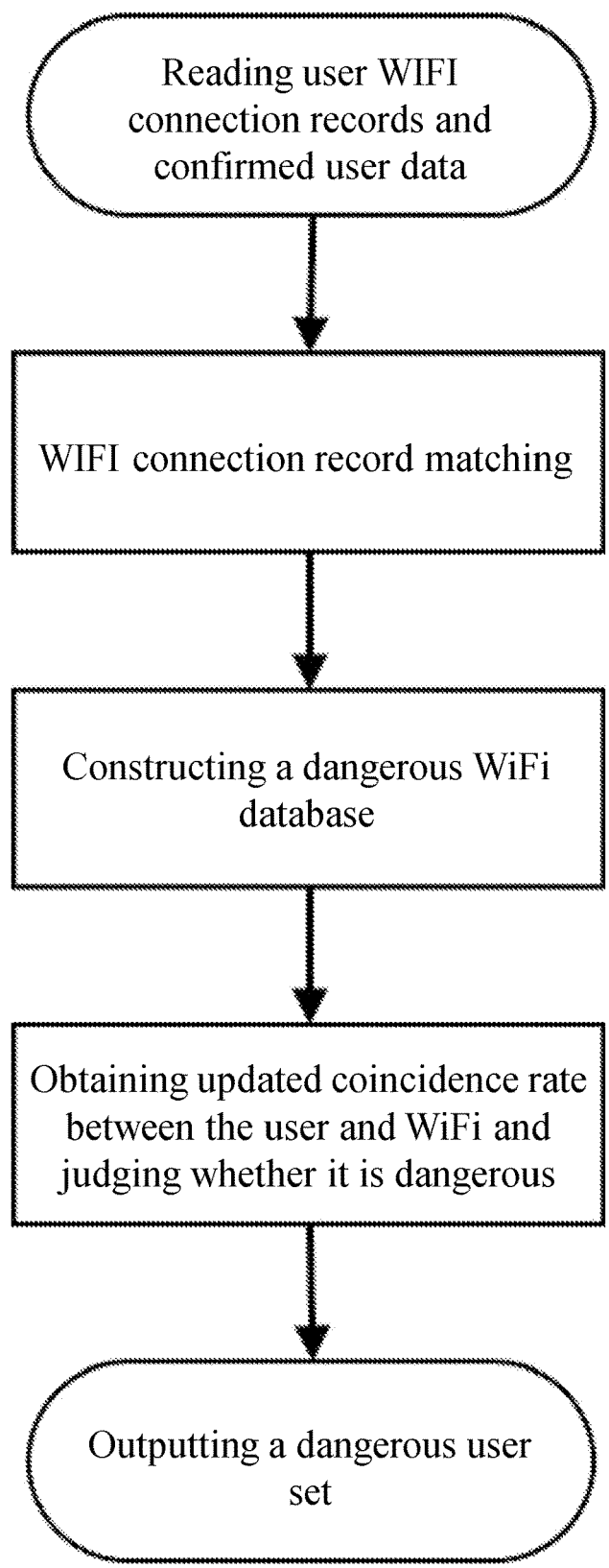
FIG. 1 is a method flow chart of digital contact tracing pre-screening based on WiFi matching of the present invention.

Below in conjunction with the accompanying drawings, the specific implementation methods and working principles of the present invention are described in detail as follows:

EMBODIMENT

In this embodiment, user WiFi connection record data collected from Jan. 1, 2020 to Mar. 20, 2020 from a certain place and anonymous information of confirmed users having a respiratory infectious disease within this time period are utilized. Specific variables and related data information included in a data set are shown in Table 1, Table 2, Table 3, and Table 4:

TABLE 1

WiFi connection record data of part of users in a certain place

| gid | hour | MAC | times | day | area |

TABLE 2

Field description of WiFi connection record data of part of users in a certain place

| Field name | Data type | Description |
| --- | --- | --- |
| | | A user anonymous identification code |
| | | A time period when a record is generated |
| | | A MAC address of a connected WiFi |
| | | The number of times that the WiFi is connected during the record generation period |
| | | Date in which the record is generated |
| | | An area code of an area that the record belongs to |

TABLE 3

National confirmed user data

| confirm_gid | confirm_day | day |
| --- | --- | --- |

TABLE 4

Field explanation of wifi_list variable in the mobile device dataset

| Field name | Data type | Description |
| --- | --- | --- |
| | | An anonymous identification code of a confirmed user |
| | | Date in which the user is confirmed |
| | | Date that the record belongs to |

In this embodiment, the default implementation data set of the contact tracing pre-screening method for infectious susceptible groups is the above-mentioned WiFi connection data of users in a certain place and data of confirmed users having a certain infectious disease, and the result of the method is the obtained list of dangerous users, and its detailed implementation steps are as follows:

1) matching the WiFi connection records according to the anonymous identification codes of the users, and using the hive sql tool to extract a sub-table from the national user WiFi connection record master table according to the record date and a selected area code to improve the matching efficiency, and taking a filtering condition as the same anonymous identification code of the users, keeping the user anonymous identity code, MAC address of the connected WiFi, record generation date, user confirmed date fields in the corresponding record, and using the record generation date as the partition index to partition the generated WiFi connection record data table of the confirmed users. In order to verify the prediction effect, in this embodiment, records of some healthy users are sampled for the same processing, and the field of the confirmed date of the healthy users is processed by default. At the same time, adding a seed field to the table. Seed equal to 0 means a healthy user, and seed equal to 1 means a confirmed user.

2) using the WiFi connection record data table of the confirmed users obtained in step 1) to process in order by date. After reading the data, extracting its gid column and MAC address column respectively, constructing a two-way mapping dictionary $dict_{user}$ and $dict_{wifi}$ respectively, and compressing the gid string and MAC address string. The compressed data table is shown in Table 5:

TABLE 5

Data table compressed by a two-way mapping dictionary

| gid | MAC | times | quezhen_date | seed |
| --- | --- | --- | --- | --- |

3) processing historical data, examining the WiFi connections of all confirmed users, and considering that a certain infectious disease has an incubation period, that is, after infection, it is asymptomatic until the diagnosis is confirmed, and if the date of record generation is within the confirmed date $T_{inc}$, adding the MAC address of the WiFi and the corresponding current date to the dangerous WiFi database. In this embodiment, taking $T_{inc}$ as 7 days. The obtained dangerous WiFi database is in the following form:

{'w3706696': datetime.date(2020, 3, 18),
'w3658960': datetime.date(2020, 2, 16),
'w3737021': datetime.date(2020, 3, 11),
'w3834102': datetime.date(2020, 3, 15),
'w194670': datetime.date(2020, 3, 20),
'w2787916': datetime.date(2020, 2, 23), . . . }

4) determining the daily updated data, grouping the daily updated user WiFi connection records according to the user gid, and summarizing the WiFi scanned by each user on that day, calculating the coincidence rate with dangerous WiFi, and judging, according to whether the coincidence rate is higher than the threshold $thr_{user}$, whether it is a dangerous user. In this embodiment, taking $thr_{user}$ as 0.1, and constructing the set of dangerous users on that day in the following form:

{'u46515', 'u19505', 'u12248', 'u35433', 'u19808', . . . }

5) updating the dangerous WiFi database according to the actual confirmed user information on that day, and updating the record date if it is already in the dangerous WiFi database.

6) mapping the current compressed user id back to the original user anonymous identity code, and performing key screening on these users. For example, the mapping result of user code in step 4) is as follows:

ANDROID-21010e17edd0437599c2388cd65d130b
ANDROID-c8607f33b36a40b7b17c227867fb290e
ANDROID-7e2f8561d05f468ca553ae9daa55b18c
ANDROID-018570e1daa544f082b655cf80feae54
ANDROID-cb2c78a391ac47229f2aa499d20a2a5f (7) In this embodiment, the daily precision rate and recall rate are shown in FIG. 1. Considering that the recall rate index is more important than the precision rate in infectious disease screening, the present invention can better realize the screening of dangerous persons.

Figure 2:
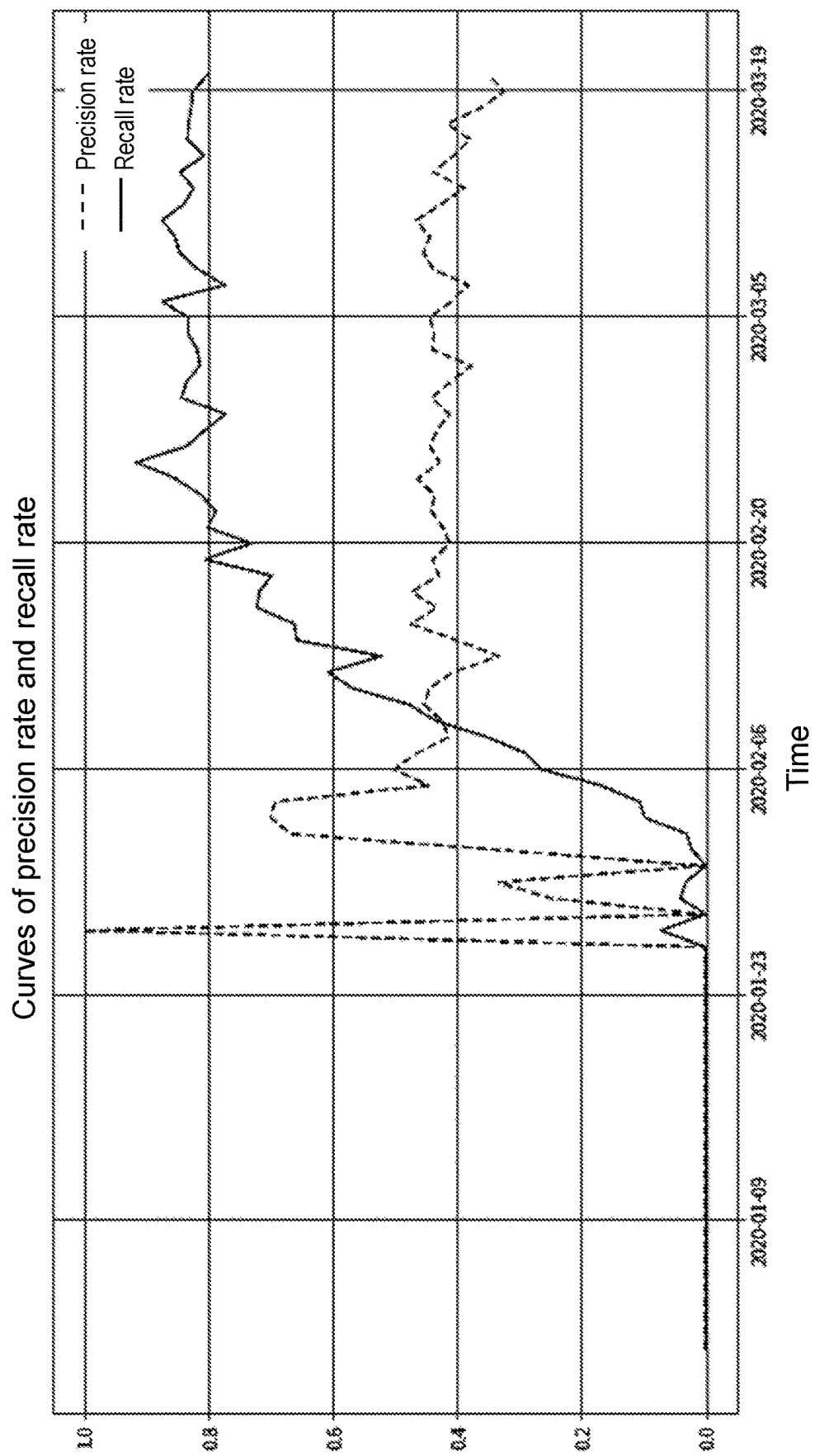
FIG. 2 is a graph showing a comparison result of a precision rate and a recall rate when screening in a user group of the embodiment of the present invention.

The present invention provides the contact tracing pre-screening method for infectious disease susceptible people based on WiFi matching. The method is mainly based on WiFi connection records of the users and the list of anonymous identification codes of the confirmed users collected by the mobile device, and finally gives the final dangerous user list through the steps of the record matching, information compression, dangerous WiFi database construction, coincidence rate calculation between the user and the dangerous WiFis, etc. FIG. 1 shows a detailed flow of the contact tracing pre-screening method for infectious disease susceptible people based on WiFi matching. The entire embodiment processes the user WiFi connection record data set according to the process shown in FIG. 1 and finally obtains the screening result of dangerous persons. FIG. 2 shows the comparison result of the precision rate and the recall rate of the screening in the user group with this method. The method analyzes, corrects and reduces the dimensions of the WiFi connection record data. Compared with the contact tracing method, it can save computing resources, reduce processing time and improve screening efficiency without involving private information such as location and without using additional equipment, which provides another data support having more comprehensive dimensions for the follow-up search for high-risk susceptible groups who may come into contact with confirmed users.

The above-mentioned embodiments are only examples of the present invention. Although the best examples of the present invention and the accompanying drawings are disclosed for the purpose of illustration, those skilled in the art can understand that: without departing from the spirit and scope of the present invention and the appended claims, various substitutions, changes and modifications are possible. Therefore, the present invention should not be limited to that disclosed in the preferred embodiments and drawings.

The invention claimed is:

1. A contact tracing pre-screening method for infectious disease susceptible people based on WiFi matching, wherein, characterized in that the method comprises following steps:

1) matching with user anonymous identification code record: obtaining a unique anonymous identification code data table of confirmed users through a database, using a hive sql tool to search for WiFi connection records corresponding to identification codes (IDs) in a total database, creating data table partitions according to dates, and saving the data table partitions as original data records with a total data time span of T days, and constructing a WiFi connection data set $R=\{R_1, R_2, \ldots, R_T\}$ of the confirmed users, wherein records of the ith day are $R_i$, and there are a total of $k_i$ records, and $R_i=\{r_{i1}, r_{i2}, \ldots, r_{ik_i}\}$, Wherein each of the records $r_{ij}=(gid_{ij}, confirmDay_{ij}, mac_{ij})$, $gid_{ij}$ represents a unique anonymous identification code of a user, $confirmDay_{ij}$ represents a confirmed date of the user, and $mac_{ij}$ represents a media access control (MAC) address of an WiFi to which the user connects;

2) pre-processing data: saving the WiFi connection data set R obtained in step (1) to local codes, and establishing a two-way mapping dictionary class, creating a new referencing symbol for any string according to a number of internal stored entries after obtaining the string, using the string and the referencing symbol respectively as a key and a value to establish a mapping; establishing a code two-way mapping dictionary $dict_{user}$ for the anonymous identification codes of the users, recording a total number of the users as $N_u$, and mapping original anonymous identification code with uniform-length of the user to a code number $u_{i_u}$, wherein $i_u=1, 2, 3, \ldots, N_u$; establishing a code two-way mapping dictionary $dict_{wifi}$ of the WiFis, recording a total number of the WiFis as $N_w$, and mapping original MAC address of the WiFi as a code number $w_{u_w}$ wherein $u_w=1, 2, 3, \ldots, N_w$; recording a record data set obtained after mapping an original record data set as R;

3) constructing a dangerous WiFi database: using the record data set R after code number mapping in step (2), recording the dangerous WiFi database as $dict_{dan}$, extracting the WiFi connection records of the confirmed users in R, taking the code number $w_{u_w}$ of the WiFi in records and putting $w_{u_{x_i}}$ in $dict_{dan}$, and recording a date in which the WiFi is recorded in the dangerous WiFi database as a current date $day_{now}$; if the WiFi already exists, updating a recording date thereof to $day_{now}$, and then deleting a record of which a difference between a recording date $day_{now}$ and the current date $day_{now}$ exceeds a dangerous WiFi disappearance threshold $thr_{dan}$;

4) judging an infection risk: recording newly acquired WiFi connection records of the users every day as $\tilde{R}$, grouping $\tilde{R}$ by the users, and for each of the users, matching all the connected WiFis thereof with $dict_{dan}$, and recording a coincidence rate as $r_{user}=|C_{user}|/|W_{user}|$, wherein $|C_{user}|$ is a number of WiFis in $dict_{dan}$ that the user connects to in that date, $|W_{user}|$ is the total number of WiFis that the user connects in that date, and if $r_{user}$ is higher than a judgment threshold $thr_{user}$, judging the user as a dangerous user.

2. The contact tracing pre-screening method for infectious disease susceptible people based on WiFi matching according to claim 1, wherein, in matching of the user anonymous identification code record in step 1), the hive sql tool is used to match an unique anonymous identification code of a confirmed user with a WiFi connection record total database of all the national users, and a data record table is generated for subsequent processing of confirmed users in the data table partitions, wherein specific implementation steps are as follows:
   1.1) forming an original database including two parts:
      1.1.1) an information data table of confirmed users, including anonymous identification codes (gid_confirm) of the confirmed users, confirmed dates (confirm_day); 1.1.2) a WiFi connection record data table of all the national users, including anonymous user identification codes (gid), connected WiFi MAC addresses (mac), record generation dates (day), record generation areas (area), record generation time (hour), and WiFi connection times (times) during the record time, using the same anonymous user identification codes of two databases as indexes, and using the hive sql tool to generate the WiFi connection record data table of the confirmed users;
   wherein, the WiFi connection record data table of all the national users is partitioned according to areas (area) and dates (day), and a target screening area and start-end time of target inspection are determined in advance when constructing a target data table;
   1.2) using the hive sql tool to partition the target data table according to dates as the indexes.

3. The contact tracing pre-screening method for infectious disease susceptible people based on WiFi matching according to claim 1, wherein, in data pre-processing of step 2), the code two-way mapping dictionary is used to compress and restore original user anonymous identification codes and the MAC addresses of the WiFis, and specific implementation steps are as follows:
   2.1) constructing the two-way mapping dictionary class (TwoWayDict), wherein after inputting an original uncompressed string, two-way mapping of uncompressed string to compressed string and the compressed string to the uncompressed string is formed inside the code two-way mapping dictionary, that is, the uncompressed string and the compressed string are stored as the key and the corresponding value respectively to save storage space and memory in subsequent processing, and, when a prediction result is obtained, the original uncompressed string is also obtained according to the code two-way mapping dictionary;
   2.2) establishing two code two-way mapping dictionaries $dict_{user}$ and $dict_{wifi}$ with the anonymous identification codes of the users and the MAC addresses of the WiFis respectively.

4. The contact tracing pre-screening method for infectious disease susceptible people based on WiFi matching according to claim 1, wherein, in constructing the dangerous WiFi database of step 3), the MAC addresses in historical user WiFi connection data are added to the dangerous WiFi database according to dates, and expired WiFis are dynamically deleted to reduce a false positive rate, wherein specific implementation steps are as follows:
   3.1) processing historical data, extracting the MAC addresses of the WiFis and confirmed dates in the WiFi connection records of historically confirmed users, and putting the MAC addresses and the confirmed dates into the dangerous WiFi database $dict_{dan}$, wherein $dict_{dan}$ takes the MAC address of the WiFi as the key and the confirmed date as the value, and, if there are duplicate MAC addresses, one date having most recent date is selected and saved as the value;
   3.2) processing daily updated data: after obtaining the daily updated data, adding the MAC addresses of the WiFis to which the confirmed users connects in that date in $dict_{dan}$ through the above method, and traversing $dict_{dan}$ after addition is complete; and if a difference between the confirmed date corresponding to the MAC address and the current date exceeds the dangerous WiFi disappearance threshold $thr_{dan}$, deleting the MAC address from the dangerous WiFi database.

5. The contact tracing pre-screening method for infectious disease susceptible people based on WiFi matching according to claim 1, wherein, in judging the infection risk of step 4), daily updated user WiFi connection data is compared with the dangerous WiFi database to obtain the coincidence rate, and a judgment is made on whether a dangerous user exists according to the judgment threshold, wherein specific steps are as follows:
   4.1) after obtaining the daily updated user WiFi connection data, grouping according to the anonymous identification codes of the users, and calculating the coincidence rate between the WiFi connection in that date and the dangerous WiFi database, wherein a calculation formula for the coincidence rate $r_{user}$ of the user (user) is as follows:

$$C_{user} = W_{user} \cap W_{dan}$$

$$r_{user} = \frac{|C_{user}|}{|W_{user}|}$$

wherein $W_{user}$ is the WiFi connected by the user in that date, and $W_{dan}$ is the dangerous WiFi database, $|S|$ represents a number of elements in a set S;
if $R_{user}$ is higher than the judgment threshold $thr_{user}$, judging $R_{user}$ as a dangerous user, and carrying out key screening.

* * * * *